US007011628B2

(12) United States Patent
LiDonnici (10) Patent No.: US 7,011,628 B2
(45) Date of Patent: Mar. 14, 2006

(54) METHODS AND DEVICES FOR MINIMIZING THE LOSS OF BLOOD THROUGH A SEVERED STERNUM DURING CARDIAC AND/OR THORACIC SURGERY

(76) Inventor: Leslie LiDonnici, 501 Hicks St., Brooklyn, NY (US) 11231

( * ) Notice: Subject to any disclaimer, the term of this patent is extended or adjusted under 35 U.S.C. 154(b) by 7 days.

(21) Appl. No.: 10/804,335

(22) Filed: Mar. 19, 2004

(65) Prior Publication Data
US 2004/0186354 A1  Sep. 23, 2004

Related U.S. Application Data

(60) Provisional application No. 60/456,303, filed on Mar. 20, 2003.

(51) Int. Cl.
*A61B 1/32* (2006.01)
(52) U.S. Cl. ...................................... 600/210
(58) Field of Classification Search ................ 600/210, 600/201, 203, 217, 219, 220, 221, 222, 235
See application file for complete search history.

(56) References Cited

U.S. PATENT DOCUMENTS

| | | | | |
|---|---|---|---|---|
| 2,238,563 A | * | 4/1941 | Jacques | 27/21.1 |
| 4,627,421 A | * | 12/1986 | Symbas et al. | 600/232 |
| 4,813,416 A | | 3/1989 | Pollak et al. | |
| 5,772,583 A | * | 6/1998 | Wright et al. | 600/232 |
| 5,823,946 A | | 10/1998 | Chin | |
| 6,033,425 A | | 3/2000 | Looney et al. | |
| D440,268 S | * | 4/2001 | Colon | D21/776 |
| 6,217,580 B1 | | 4/2001 | Levin | |
| 6,273,853 B1 | | 8/2001 | Cartier et al. | |
| 6,358,270 B1 | | 3/2002 | Lemer | |
| 6,368,342 B1 | | 4/2002 | Lemer | |
| 6,540,769 B1 | | 4/2003 | Miller, III | |
| 2002/0120177 A1 | | 8/2002 | Borst et al. | |
| 2003/0153947 A1 | | 8/2003 | Koseki | |
| 2004/0010256 A1 | | 1/2004 | Gabbay | |

OTHER PUBLICATIONS

Copy of Literature entitled "Sternal Retractors and Rib Spreaders", pp. 1.

* cited by examiner

*Primary Examiner*—Eduardo C. Robert
*Assistant Examiner*—David Comstock
(74) *Attorney, Agent, or Firm*—Carter, Deluca, Farrell & Schmidt, LLP (57) ABSTRACT

The present disclosure relates to methods and devices for stanching the effusion of blood from the exposed ends of the sternal halves of an incised sternum during cardiac and/or thoracic surgical procedures. According to an aspect, there is provided a device for stanching the effusion of blood from an exposed sternal half of a sternum formed during a sternotomy. The device includes an end wall having a size and a dimension to at least partially cover the exposed end of a sternal half. The device may include an upper wall; a lower wall spaced from the upper wall; and an end wall interconnecting the upper and lower walls. The upper wall, the lower wall and end wall bound a space while the upper wall and the lower wall define an opening through which an exposed end of a sternal half is receivable into the space of the device.

19 Claims, 10 Drawing Sheets

METHODS AND DEVICES FOR MINIMIZING THE LOSS OF BLOOD THROUGH A SEVERED STERNUM DURING CARDIAC AND/OR THORACIC SURGERY

CROSS REFERENCE TO RELATED APPLICATIONS

The present application claims the benefit of and priority to U.S. Provisional Application Ser. No. 60/456,303, filed on Mar. 20, 2003, the entire content of which is incorporated herein by reference.

BACKGROUND

1. Technical Field

The present disclosure relates generally to methods and devices associated with cardiac and/or thoracic surgery and, more particularly, to methods and devices for minimizing the loss of blood through a severed sternum during cardiac and/or thoracic surgical procedures.

2. Background of Related Art

A full median sternotomy is probably the most common procedure performed today for providing surgical access to the heart and coronary arteries. A sternotomy, however, is highly invasive. The patient's skin is incised at the midline overlying the chest and the patient's sternum is cut, using a saw or other comparable cutting instrument, along at least a portion, typically, along its entire length. The cut edges of the sternum are then spread with metal retractors, exposing a large cavity to allow surgery to be performed on the heart. Generally, such retractors use two substantially perpendicular retractor blades that remain generally at the same height in their operative position.

The retractor blades are then manipulated (e.g., spread apart) an amount sufficient to create an opening in the thoracic cavity which is large enough through which a surgeon may directly visualize and operate upon the heart and the other thoracic organs or tissue. Following such a procedure, the two severed sternal halves must be reapproximated, i.e., the sternum is rejoined and closed securely using known surgical techniques and devices.

The sternotomy typically results in the effusion or loss of blood, at times severe and at other times quite excessive, during the surgical procedure. This loss of blood may obstruct and at times may obliterate the view of the surgical team when performing the surgical procedure.

Recently, waxes, gels and the like have been developed to be applied to the bleeding surfaces of the sternum halves following the cutting of the sternum. These substances include compositions (e.g., astringents and the like) which help to inhibit and/or otherwise reduce the effusion of blood. It would be beneficial if these substances could be removed from the sternum halves and, more importantly, from the thoracic cavity, following the surgical procedure. However, the current state of the art is lacking in this regard. These substances are left in the sternum (i.e., between the sternal halves) following the surgical procedure, and cause contamination of the blood cells which may lead to additional post operative procedures and treatments. Also, these substances have proven to be less than effective in performing their intended function, i.e., inhibiting the effusion of blood.

Accordingly, a continuing need exists for improved methods and devices for minimizing the loss of blood through a severed sternum during cardiac and/or thoracic surgical procedures.

The need exists for devices which may be removably placed over an exposed end of each sternal half prior to use of a conventional retractor.

SUMMARY

The present disclosure relates to methods and devices for stanching the effusion of blood from the exposed ends of the sternal halves of an incised sternum during cardiac and/or thoracic surgical procedures.

According to one aspect of the present disclosure, there is provided a device for stanching the effusion of blood from an exposed sternal half of a sternum formed during a sternotomy. The device includes an end wall having a size and a dimension to at least partially cover the exposed end of a sternal half, wherein the device stanches the effusion of blood from the exposed end of the sternal half.

The device further includes an upper wall integrally formed with and extending orthogonally from an upper edge of the end wall; and a lower wall integrally formed with and extending orthogonally from a lower edge of the end wall. The end wall may include a rounded first and second end. The upper wall and the lower wall may extend along the first and second ends of the end wall. The upper wall and the lower wall define a continuous wall around the perimeter of the end wall.

The device may further include anchoring structure extending from the end wall. The anchoring structure may include at least one spike protruding from a surface of the end wall to contact the exposed end of the sternal half. The spikes may be removably connected to the end wall.

The device may further include a wall extending around at least a portion of the end wall. The end wall may be fabricated from at least one of plastic, stainless steel and/or titanium.

According to another aspect of the present disclosure, a device for stanching the effusion of blood from an exposed sternal half of a longitudinally divided sternum, formed during a sternotomy, is provided. The device includes an upper wall; a lower wall spaced from the upper wall; and an end wall interconnecting the upper and lower walls. The upper wall, the lower wall and end wall bound a space. The upper wall and the lower wall define an opening through which an exposed end of a sternal half is receivable into the space of the device.

The device may have a "C-shaped" or a "U-shaped" transverse cross-sectional profile, wherein the surface contacting the exposed end of the sternal half is substantially flat. The upper wall, the lower wall and the end wall desirably has a radius of curvature of about 8.625 inches. The upper wall has a thickness of about 0.1875 inches. The lower wall has a thickness of about 0.0625 inches. The device may be fabricated from a plastic.

The device may further include a first and a second terminal end. The terminal ends may be arcuate. Desirably, the space between the upper and lower walls of the device has a height of about 0.75 inches.

According to another aspect of the present disclosure, a method of minimizing the effusion of blood from the exposed ends of a sternal half of a longitudinally divided sternum, formed during a sternotomy, is provided. The method includes the steps of providing a pair of devices for stanching the effusion of blood from the exposed ends of the sternal halves; and placing a device against each exposed end of each sternal half. The devices are disposed between the exposed end of each sternal half and a blade of a surgical retractor.

Each device may include an upper wall; a lower wall spaced from the upper wall; and an end wall interconnecting the upper and lower walls. The upper wall, the lower wall and end wall bound a space. The upper wall and the lower wall define an opening through which the sternal half is receivable into the space of the device. Each device may have a substantially C-shaped transverse cross-section profile, wherein the surface of the device in contact with the exposed end of the sternal half is substantially flat. Each device may be fabricated from plastic, stainless steel and/or titanium.

The method may further include the step of imaging or estimating the size of the sternum to determine the size of the device required for the surgical procedure. The method may further include the steps of placing the blades of a surgical retractor, when in an approximated position, between the devices placed over the exposed ends of the sternal halves; and manipulating the retractor to separate the blades of the surgical retractor and spread the sternal halves apart.

In a sternotomy wherein the sternum of a patient has been longitudinally incised along at least a portion thereof, thereby exposing and allowing two opposing sternal halves to be separated laterally, the improvement includes the step of providing a pair of caps for stanching the effusion of blood from the exposed sternal halves of the sternum. Each cap including an upper wall; a lower wall spaced from the upper wall; and an end wall interconnecting the upper and lower walls. The upper wall, the lower wall and end wall bound a space. The upper wall and the lower wall define an opening through which the sternal half is receivable into the space of the cap. The improvement further includes placing a cap on each exposed sternal half such that the sternal half is received in the space of the cap.

Each cap may be fabricated from plastic, stainless steel and/or titanium.

The method further includes the steps of placing the blades of a surgical retractor, when in an approximated position, between the caps placed over the exposed ends of the sternal halves; and manipulating the retractor to separate the blades of the surgical retractor and spread the sternal halves apart. Each cap may include at least one spike extending from the end wall thereof.

The method may further include the steps of providing clips for guiding and securing the caps against the exposed ends of the sternal halves; and placing the clips over the caps and into engagement with the sternal halves.

Other objects and further scope of the applicability of the present invention will become apparent from the detailed description to follow, taken in conjunction with the accompanying drawings wherein like parts are designated by like reference numerals.

BRIEF DESCRIPTION OF THE DRAWINGS

The foregoing and other aspects of the present invention will best be appreciated with reference to the detailed description of the invention in conjunction with the accompanying drawings, wherein.

DETAILED DESCRIPTION OF PREFERRED EMBODIMENTS

Devices and methods of using the devices according to the present disclosure are provided to be used with a sternum retractor or the like. While the structure and use of various embodiments of the device of the present disclosure are discussed in detail below, it should be appreciated that the present disclosure provides for inventive concepts capable of being embodied in a variety of specific contexts. The specific embodiments of the devices discussed herein are merely illustrative of their specific construction and of their specific method of using and are not to be interpreted as limiting the scope of the instant disclosure. While the devices and methods will be described with a certain degree of particularity, it will be clear that changes may be made in the details of construction and/or sequence of use without departing from the spirit and scope of this disclosure. It is further understood that the description of the devices set forth below is not to be limited to those embodiments, and that additional embodiments may be appreciated by one of skill in the art.

Referring initially to FIGS. 1–4, wherein like reference numerals refer to like elements, according to a first embodiment of the present disclosure, a device, cuff or cap, for stanching the effusion of blood from an exposed end of a sternal half, is designated as 100. Device 100 includes a planar wall 106 surrounded by a perimetral wall defined by an upper wall 102, a lower wall 104, a first side end wall 112, and a second side end wall 114. The perimetral wall bounds a space 110 and defines an opening 116 to space 110. Preferably, end walls 112 and 114 are rounded.

Figure 4:
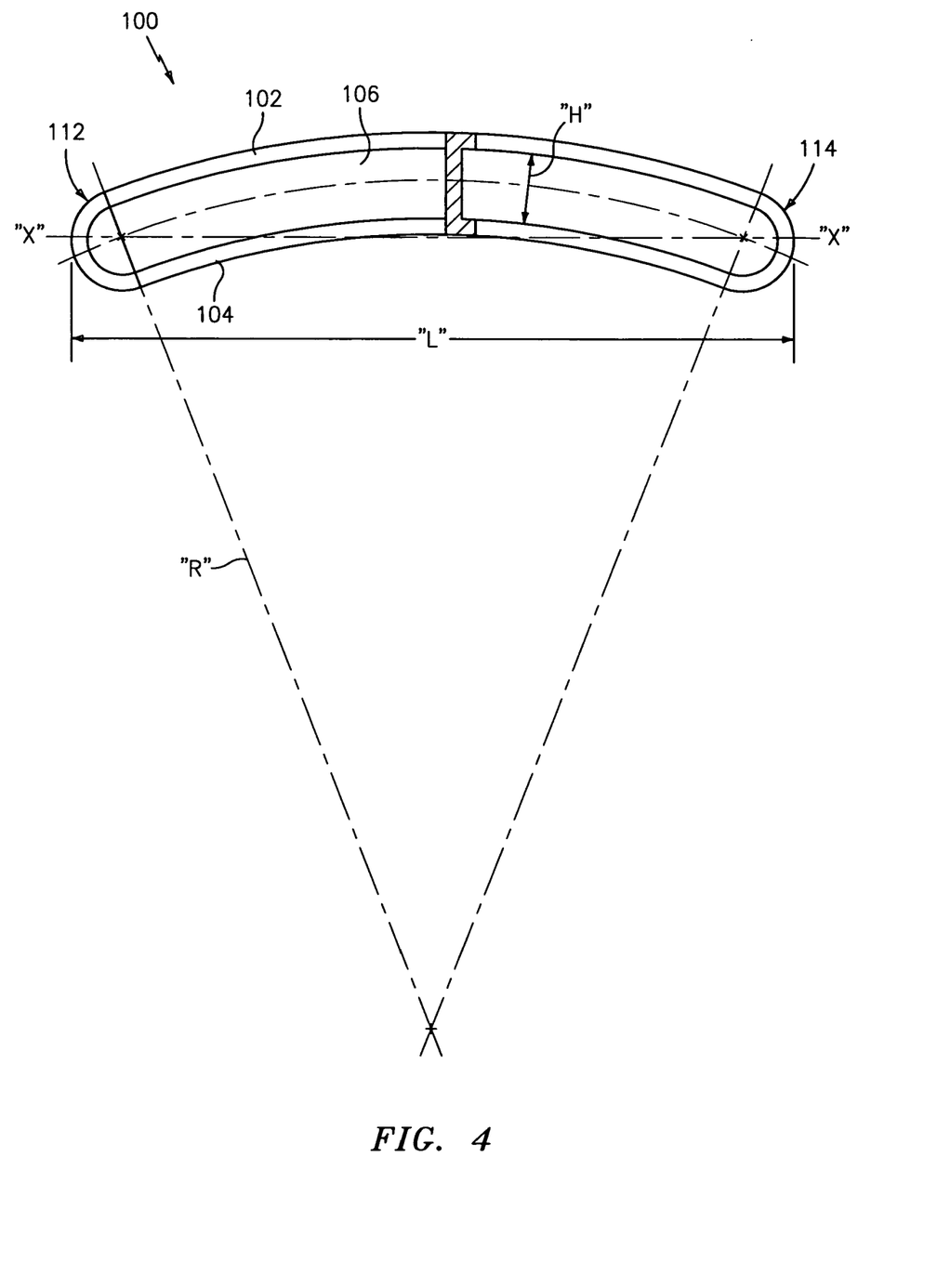
FIG. 4 is a front elevational view of the device of FIGS. 1–3.

Preferably, as seen in FIG. 4, upper wall 102 has a thickness of about 0.1875 inches and lower wall 104 has a thickness of about 0.0625 inches. While device 100 has been shown and described as including an upper wall 102 and a lower wall 104 having different thicknesses, it is envisioned and within the scope of the present disclosure for upper and lower walls 102 and 104 to have a uniform thickness throughout.

Device 100 has an overall length "L" (see FIG. 4) which is preferably larger than the length of the exposed end surface of a sternal half of a longitudinally divided sternum. Preferably, device 100 has a length "L" which is from about 5.0 inches to about 8.0 inches, most preferably, about 6.6875 inches. Desirably, device 100 has a length "L" which is greater than the width of a blade of a surgical retractor.

Figure 1:
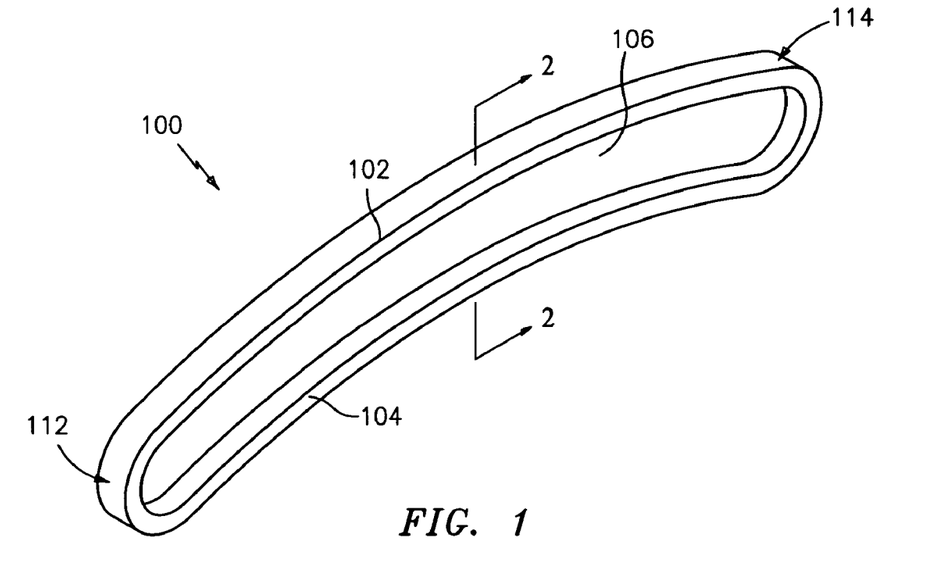
FIG. 1 is a perspective view of a device, according to an embodiment of the present disclosure, for covering an exposed end of a sternal half of a longitudinally divided sternum.
Figure 2:
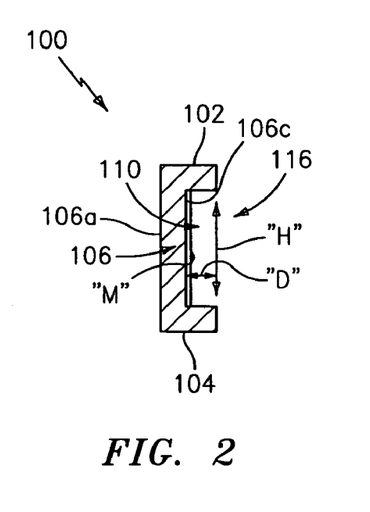
FIG. 2 is a cross-sectional side elevational view of the device of FIG. 1, as taken through 2—2 of FIG. 1.

As best seen in FIG. 2, space 110 of device 100 has a height "H" (prefreably greater than the height of the exposed end of the sternal half) and a depth "D". Preferably, space 110 has a height "H" of about 0.75 inches and a depth "D" of about 0.0625 inches.

Figure 2A:
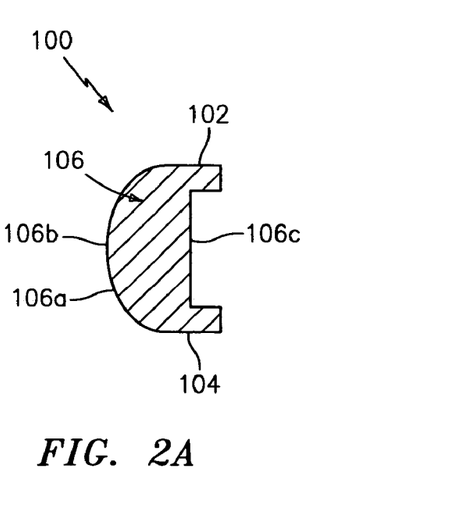
FIG. 2A is a cross-sectional side elevational view of the device of FIG. 1, as taken through 2—2 of FIG. 1, illustrating another cross-sectional profile for the device of FIG. 1.
Figure 3:
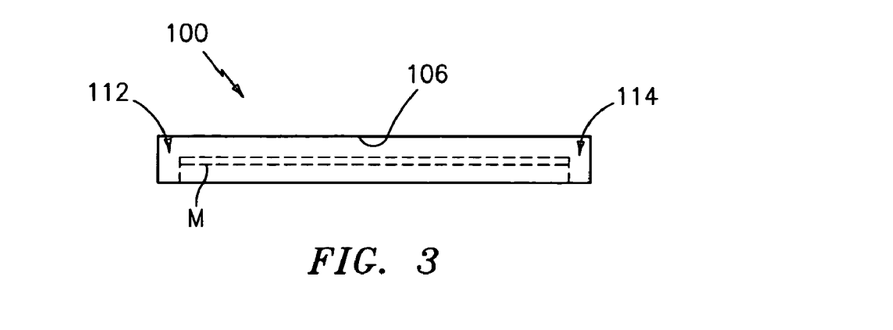
FIG. 3 is a top plan view of the device of FIGS. 1 and 2.

As seen in FIG. 2, device 100 may include a substantially flat rear surface 106a, or as seen in FIG. 2A, device 100 may include an arcuate rear surface 106b. Additionally, as seen in FIGS. 2 and 2A, device 100 preferably includes a front surface 106c, disposed between upper and lower walls 102, 104 and opposite rear surface 106a or 106b. Preferably, front surface 106c is at least substantially flat along the entire surface thereof in order to best contact the exposed end surface of sternal halves "S1" and/or "S2".

As best seen in FIG. 4, device 100 defines a longitudinal axis "X". Device 100 and, more particularly, upper and lower walls 102, 104 and end wall 106 are curved along at least a portion of the, preferably along the entire, length thereof. Device 100 has a radius of curvature "R" of about 8.625 inches. While it is desirable for device 100 to be curved along at least a portion of the length thereof, it is envisioned and within the scope of the present disclosure for device 100 to be substantially linear along the entire length thereof. Accordingly, as seen in FIG. 4, device 100 has a kidney-like or bean-like foot print.

Device 100 is preferably fabricated from a polycarbonate material, such as, for example, Lexan. While device 100 is preferably fabricated from a polycarbonate material, it is envisioned and within the scope of the present disclosure that device 100 may be fabricated from other biologically compatible and/or biologically inert materials, such as, for example, polyethylene, polypropylene, other polymeric materials, stainless steel, titanium and the like. Preferably, device 100 is fabricated from a material which may be autoclaved for reuse.

Figure 5:
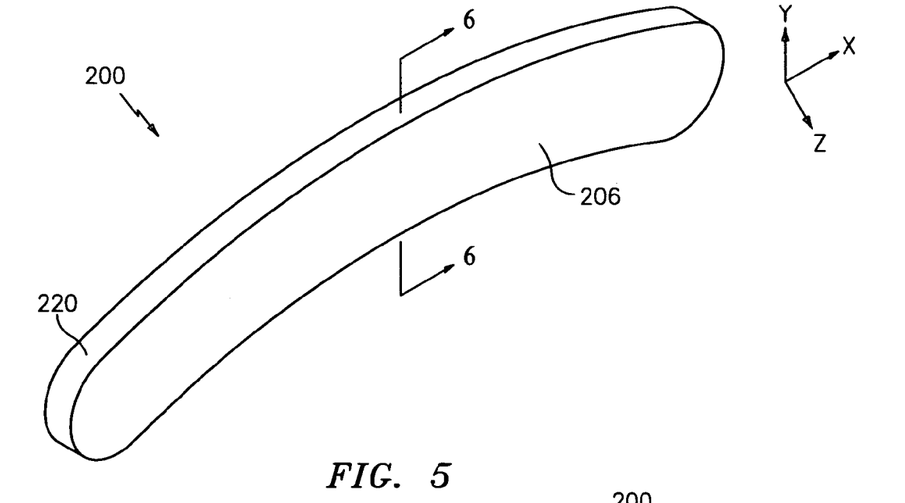
FIG. 5 is a perspective view of a device for covering an exposed end of a sternal half of a longitudinally divided sternum, according to an alternate embodiment of the present disclosure.
Figure 6:
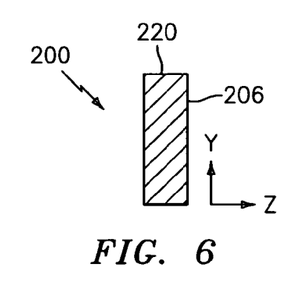
FIG. 6 is a cross-sectional side elevational of the device of FIG. 5, as taken through 6—6 of FIG. 5.
Figure 7:
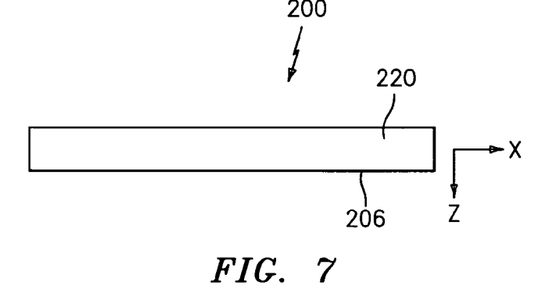
FIG. 7 is a top plan view of the device of FIGS. 5 and 6.

Turning now to FIGS. 5–7, a device, for stanching the effusion of blood from an exposed end of a sternal half, is designated as 200. Device 200 is similar to device 100 and will only be described to the extent necessary to identify differences in construction and operation.

Device 200 includes a planar wall 206 having an outer terminal edge 220. Device 200 has a substantially kidney-shaped or bean-shaped foot print. As seen in FIGS. 6 and 7, while device 200 is substantially planar in both a longitudinal (X-direction) and a transverse (Y or Z-direction) direction, it is envisioned and within the scope of the present disclosure that device 200 may be curved in the longitudinal and/or transverse directions.

Figure 8:
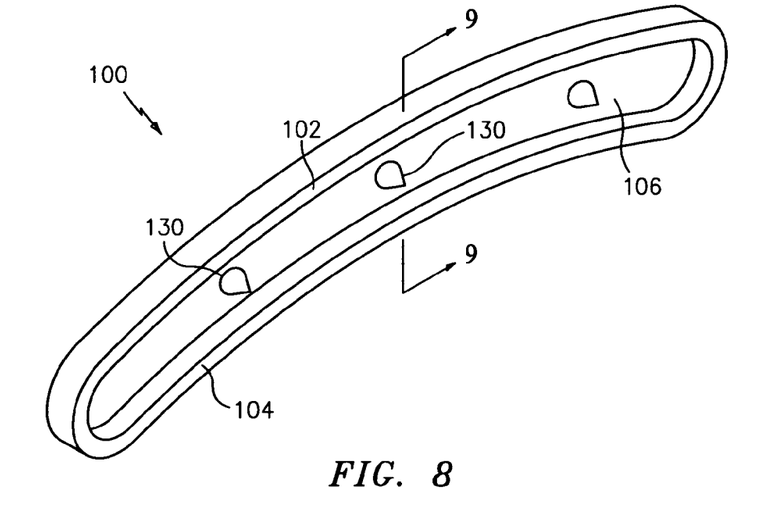
FIG. 8 is a perspective view of a device for covering an exposed end of a sternal half of a longitudinally divided sternum, according to yet another embodiment of the present disclosure.
Figure 9:
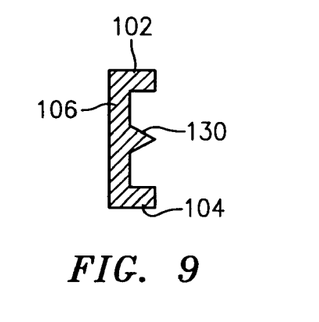
FIG. 9 is a cross-sectional side elevational view of the device of FIG. 8, as taken through 9—9 of FIG. 8, illustrating an embodiment of an anchoring structure extending therefrom.

Turning now to FIGS. 8–11, anchoring structure, for fixing the position of device 100 against the exposed end of the sternal half, are shown and described. As seen in FIGS. 8 and 9, the anchoring structure includes at least one spike 130 extending from the surface of end wall 106. Preferably, spikes 130 are integrally formed with and/or monolithically formed with end wall 106.

Figure 10:
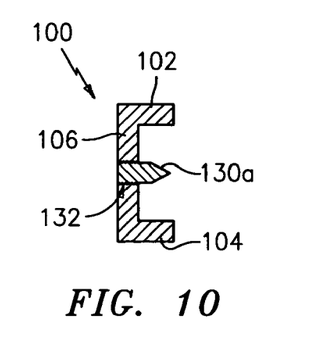
FIG. 10 is a cross-sectional side elevational view of the device of FIG. 8, as taken through 9—9 of FIG. 8, illustrating another embodiment of an anchoring structure extending therefrom.

As seen in FIG. 10, the anchoring structure may take the form of threaded spikes 130a which are threadingly received in apertures 132 formed in end wall 106.

Figure 11:
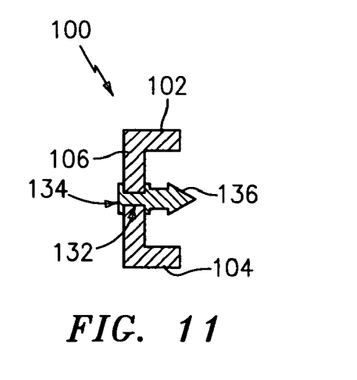
FIG. 11 is a cross-sectional side elevational view of the device of FIG. 8, as taken through 9—9 of FIG. 8, illustrating yet another embodiment of an anchoring structure extending therefrom.

As seen in FIG. 11, the anchoring structure may take the form of barbed spikes 130b having an inter-engaging proximal end 134, which is received in an aperture 132 formed in end wall 106, and an arrowhead-shaped distal end 136.

Desirably, the anchoring structure (e.g., spikes 130, 130a and 130b) is secured to and/or otherwise integrally formed with end wall 106 in such a manner that the anchoring structure will not break away or otherwise separate from end wall 106.

Figure 12:
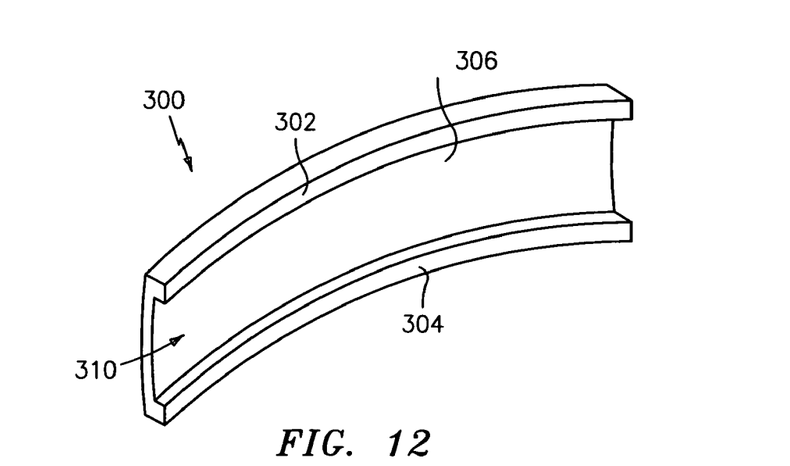
FIG. 12 is a perspective view of a device for covering an exposed end of a sternal half of a longitudinally divided sternum, according to still another embodiment of the present disclosure.

Turning now to FIG. 12, an alternate embodiment of a device for stanching the effusion of blood from an exposed end of sternal half, is designated as 300. Device 300 includes an end wall 306 having an upper wall 302 and a lower wall 304. Upper wall 302, lower wall 304 and end wall 306 define an open ended channel 310 having a substantially "C-shaped" or "U-shaped" transverse cross-sectional profile, wherein a surface of device 300 in contact with the exposed end of the sternal half is at least substantially flat. Preferably, upper wall 302 and lower wall 304 extend along at least a portion of the length of end wall 306.

Figure 13:
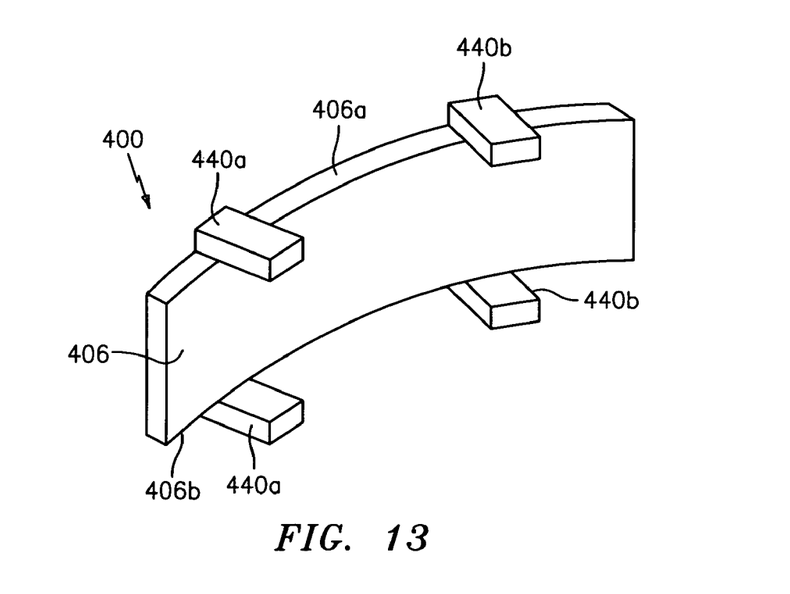
FIG. 13 is a perspective view of a device for covering an exposed end of a sternal half of a longitudinally divided sternum, according to yet another embodiment of the present disclosure.

As seen in FIG. 13, yet another embodiment of a device for stanching the effusion of blood from an exposed end of a sternal half, is designated as 400. Device 400 includes an end wall 406 having an upper terminal edge 406a and a lower terminal edge 406b. Device 400 includes at least one, preferably a pair of, arms or guides 440a, 440b extending transversely from each of upper terminal edge 406a and lower terminal edge 406b. Arms 440a, 440b act to guide device 400 onto and against the exposed end of the sternal half.

Figure 14:
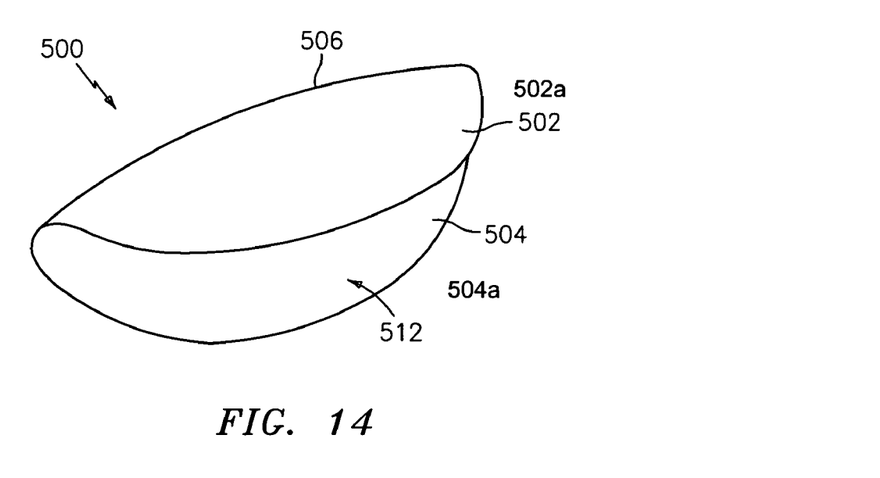
FIG. 14 is a perspective view of a device for covering an exposed end of a sternal half of a longitudinally divided sternum, according to still another embodiment of the present disclosure.
Figure 15:
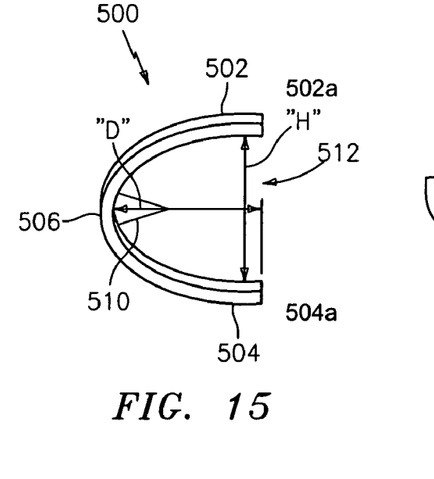
FIG. 15 is a cross-sectional side elevational view of the device of FIG. 14.
Figure 16:
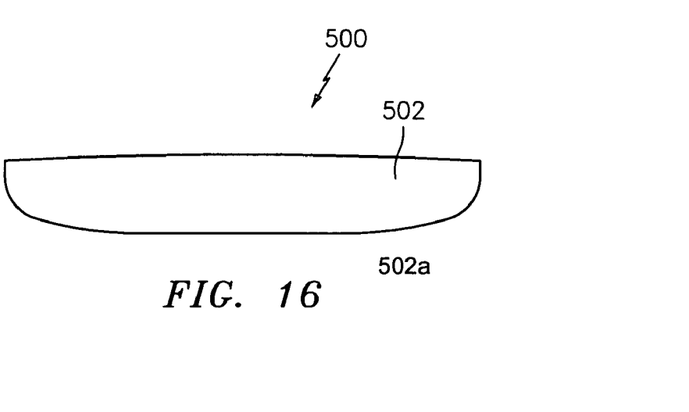
FIG. 16 is a top plan view of the device of FIGS. 14 and 15.

Referring now to FIGS. 14–17, a device for stanching the effusion of blood from an exposed end of a sternal half, according to still another embodiment of the present disclosure, is designated as 500. As seen in FIGS. 14 and 15, device 500 has a substantially "C-shaped" or "U-shaped" transverse cross-sectional profile. Device 500 includes a pair of juxtaposed walls, namely, an upper wall 502 and a lower wall 504, interconnected by an end or base wall 506. Upper and lower walls 502, 504 and end wall 506 bound a space 510. Meanwhile, upper and lower walls 502, 504 define an opening 512 therebetween.

Device 500 further defines a first and second terminal end 502a, 504a. Preferably, terminal ends 502a, 504a are curved to thereby provide a smooth transition from upper and lower walls 502, 504 to end wall 506. While first and second terminal ends 502a, 504a are preferably curved, it is envisioned and within the scope of the present disclosure that first and second terminal ends 502a, 504a may be flattened, truncated or otherwise defined.

Desirably, device 500 is fabricated from a material having a degree of flexibility such that upper wall 502 and lower wall 504 may be spread apart from one another to conform to the needs of the particular surgical procedure.

It is envisioned and within the scope of the present disclosure that the surface of the sternal half capping devices, which is to contact the exposed surface of the sternal half, may be provided with and/or otherwise coated with a medicament "M". (see FIGS. 2 and 3). Medicament "M" includes and is not limited to antibiotics, astringents and hemostats. It is further envisioned that medicament "M" may take the form of a gel, paste, wax or a wafer. In this manner, when the sternal half capping devices are placed over sternal halves "S1" and "S2", the effusion of blood may be further retarded.

Figure 18:
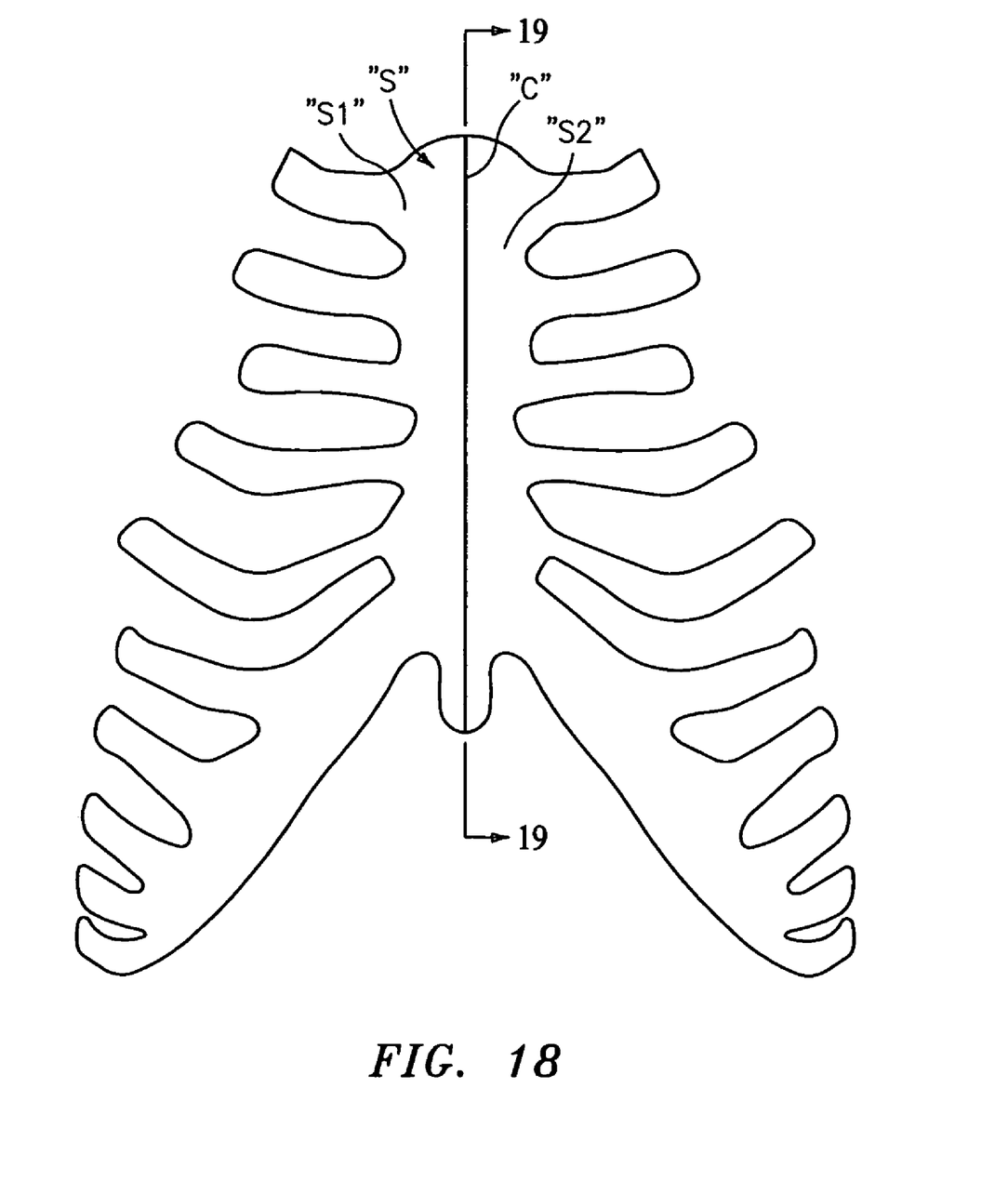
FIG. 18 is a schematic illustration of a patient's rib cage depicting the longitudinal separation of the patient's sternum.

With reference to FIGS. 18–22 a method of use of device 100 will be shown and described. As seen in FIG. 18, the sternum "S" of a patient is longitudinally divided using known surgical techniques, such as, for example, using a saw or other appropriate cutting instrument, to make a midline, longitudinal incision "C" along at least a portion of the patient's sternum "S", thereby allowing two opposing sternal halves "S1, S2" to be separated laterally.

Figure 19:
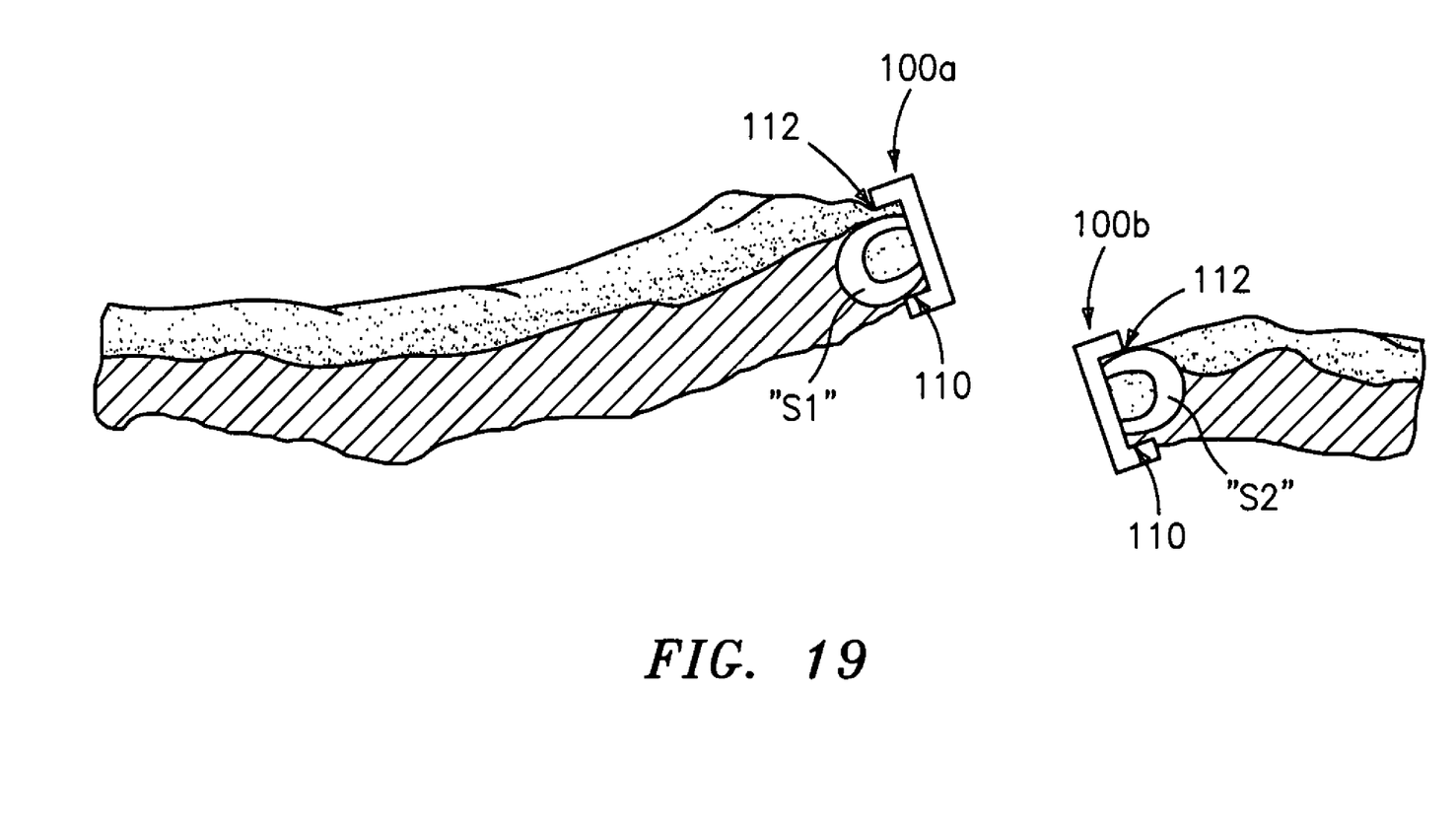
FIG. 19 is cross-sectional view of the patient's rib cage of FIG. 18, as taken through 19—19 of FIG. 18, illustrating the insertion of the device of FIGS. 1–4 between the sternal halves and onto the exposed end surfaces thereof.

Turning now to FIG. 19, with sternum "S" divided along incision "C", a first device 100a for capping the exposed end of sternal half "S1" is placed over first sternal half "S1" and a second device 100b for capping the exposed end of sternal half "S2" is placed over second sternal half "S2". In particular, first sternum capping device 100a is placed over first sternal half "S1" such that first sternal half "S1" is received in space 110 (see FIG. 2) through opening 116 (see FIG. 2). Likewise, second sternal capping device 100b is placed over second sternal half "S2" such that second sternal half "S2" is received in space 110 (see FIG. 2) through opening 116 (see FIG. 2). Each sternal capping device 100a, 100b acts to stanch the flow of blood effusing from sternal halves "S1", "S2".

Preferably, the cross-sectional profile and dimensions of sternum "S" may be quite accurately ascertained prior to the surgical procedure and/or prior to the incising of sternum "S" by means of various diagnostic procedures, including, and not limited to, X-rays, CT scans, and MRI images. This permits having for instantaneous use, properly sized and shaped sternal capping devices 100a, 100b that may be positioned over the first and second sternal halves "S1", "S2" immediately following the incising of sternum "S".

Figure 20:
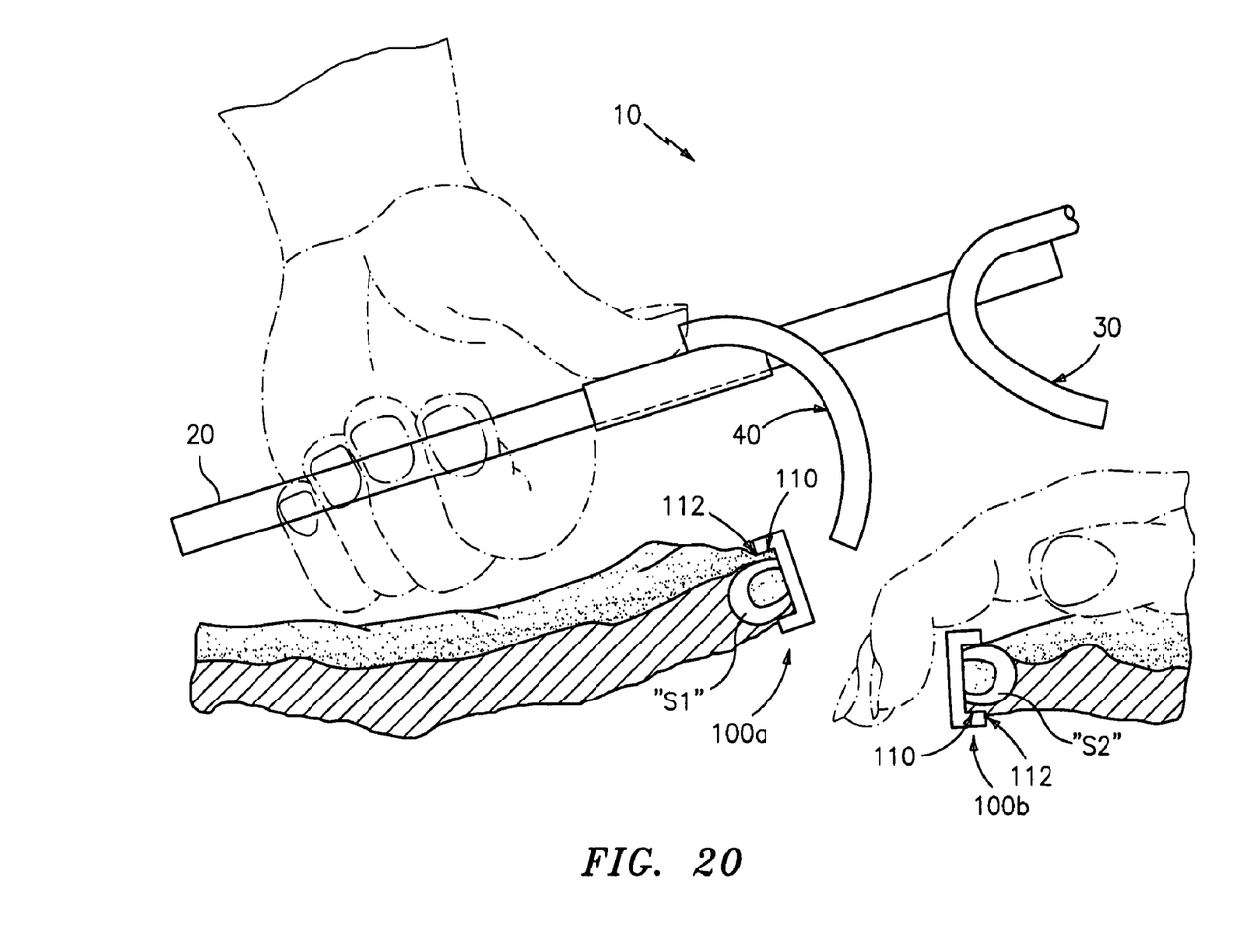
FIG. 20 is a cross-sectional view of the patient's rib cage of FIG. 18, as taken through 19—19 of FIG. 18, illustrating the insertion of a retractor between the sternal halves and into cooperating engagement with the device of FIGS. 1–4.

Turning now to FIG. 20, following placement of sternal capping devices 100a, 100b over first and second sternal halves "S1", "S2", as described above, a retractor 10 is then used to maintain a thoracic cavity access via the sternal incision "C". Briefly, retractor 10 includes a rack 20, a first blade 30 fixedly attached to rack 20, and a second blade 40 movable along a portion of rack 20. Retractor 10 further includes attaching means 50 which permits first blade 30 and second blade 40 to move between a closed position and an open position.

With first and second blades 30 and 40 of retractor 10 in the first position second blade 40 is inserted between first and second sternal halves "S1" and "S2". Sternal halves "S1" and "S2" are then separated by an amount sufficient to allow passage of first blade 30 between sternal halves "S1" and "S2". First and second sternal capping devices 100a, 100b prevent direct contact of blades 30, 40 of retractor 10 against the exposed surfaces of sternal halves "S1" and "S2". As mentioned above, sternal capping devices 100a, 100b have a length which is larger than the width of blades 30, 40 of retractor 10.

Figure 21:
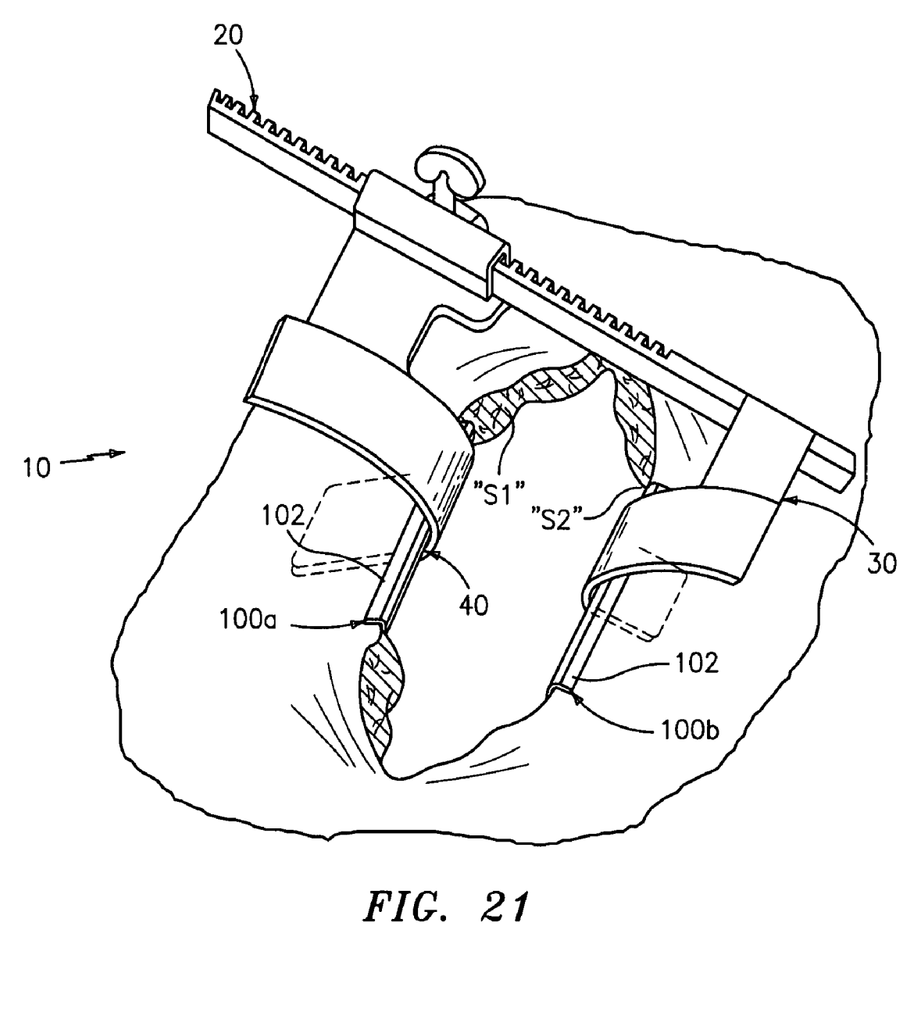
FIG. 21 is a perspective view illustrating the retraction of the sternal halves of FIG. 20 by the retractor.

As seen in FIG. 21, with blades 30, 40 of retractor 10 positioned between sternal halves "S1" and "S2", retractor 10 is operated and/or otherwise manipulated to thereby separate blades 30, 40 and, in turn, to laterally separate sternal halves "S1" and "S2" from one another. As so positioned, sternal capping devices 100a, 100b are in interposed between respective sternal halves "S1" and "S2", and blades 30, 40 of retractor 10.

It is envisioned that sternal capping devices 100 may be available in several different sizes so that the surgeon may choose those caps which are large enough to surround the cross-sectioned sternum (i.e., sternal halves "S1" and "S2") without requiring more space in the chest cavity then absolutely necessary. It is further envisioned that sternal capping devices 100 may be supplied in a pair, e.g., as a left side capping devices and a right side capping devices.

It is envisioned and within the scope of the present disclosure that sternal capping devices 100 may be specially or custom fabricated to accommodate any deformity or inconsistency in the topographical or cross-sectional profile of sternum "S".

Figure 17:
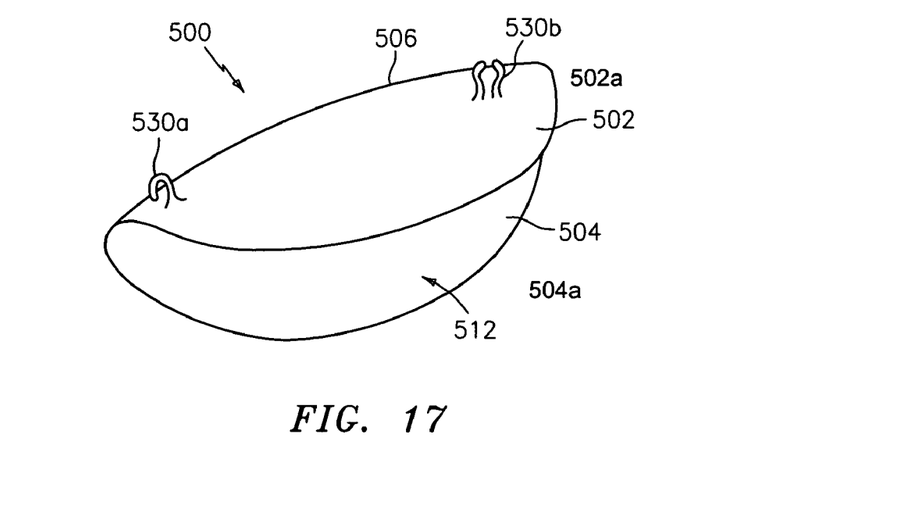
FIG. 17 is a perspective view of a device for covering an exposed end of a sternal half of a longitudinally divided sternum, according to another embodiment of the present disclosure.

As seen in FIG. 17, sternal capping device 500 may be molded or fabricated to include customized mounting pads for holding special tools, optical devices, aspirators and the like. For example, as seen in FIG. 17, sternal capping device 500 may be provided with a hook 530a or a pair of resilient fingers 530b extending from upper wall 502 thereof. Hook 530a or fingers 530b act to retain the special tools, optical devices or aspirators in a snap-fit type engagement.

Figure 22:
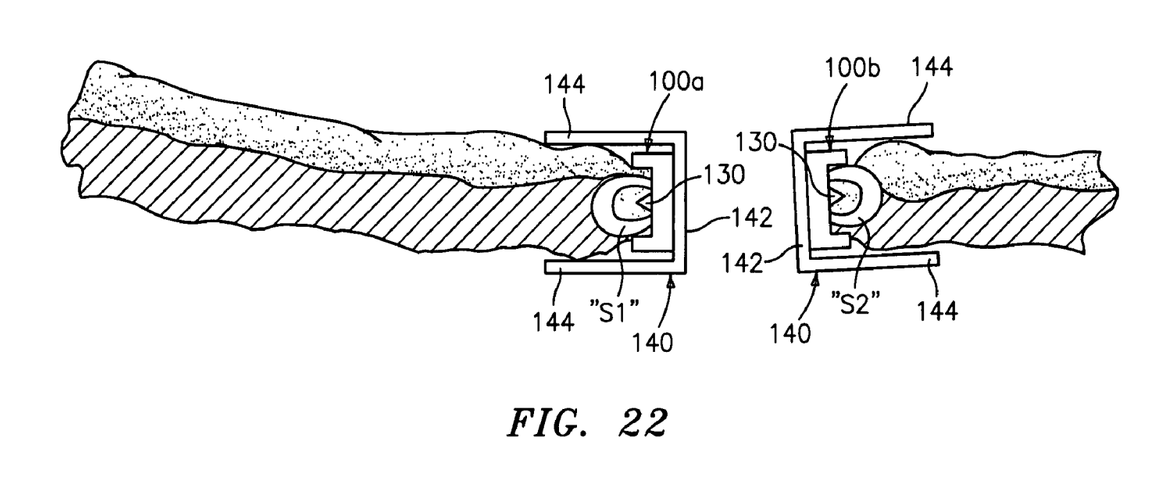
FIG. 22 is a cross-sectional view of the patient's rib cage, as taken through 19—19 of FIG. 18, illustrating the use of alignment structure to position the device of FIGS. 8–11 against the exposed end of the sternal halves.

As seen in FIG. 22, if sternal capping device 100 includes spikes 130, when sternal capping devices 100 are placed against the exposed ends of sternal halves "S1" and "S2", spikes 130 are pressed into the marrow of sternal halves "S1" and "S2". Spikes 130 help to further anchor and/or orientate sternal capping device 100 against the exposed ends of sternal halves "S1" and "S2".

In addition to or in lieu of spikes 130, as seen in FIG. 22, clips 140 may be provided which facilitate orientation and placement of sternal capping devices 100 against the exposed end of sternal halves "S1" and "S2". Clips 140 include a backspan 142 which engages sternal capping devices 100, and a pair of legs 144 extending from backspan 142 to overlie the upper and lower surfaces of sternal halves "S1" and "S2". Preferably, backspan 142 is fixedly secured to sternal capping devices 100a,100b.

Figure 23:
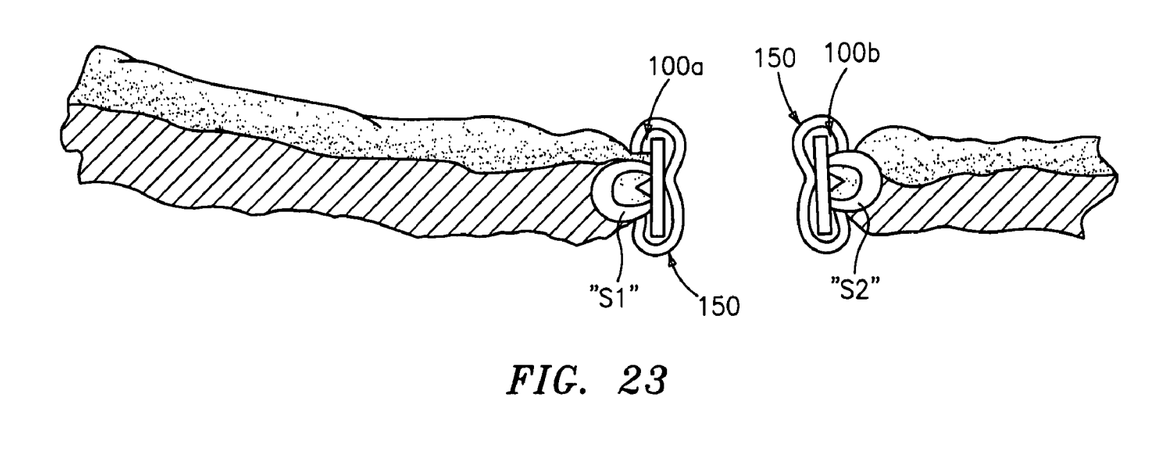
FIG. 23 is a cross-sectional view of the patient's rib cage, as taken through 19—19 of FIG. 18, illustrating the use of clips to position the device of FIGS. 8–11 against the exposed end of the sternal halves.

Turning now to FIG. 23, in addition to or in lieu of spikes 130, spring clips 150 may be provided to fix and/or otherwise anchor sternal capping devices 100a, 100b against the respective exposed end surface of sternal halves "S1" and "S2". Preferably, clips 150 are configured such that the legs thereof wrap around sternal capping devices 100a, 100b and engage and/or contact the exposed sternal half along an upper and lower surface thereof. Preferably, clips 150 are configured such that the backspan thereof contacts and/or presses against the surface of sternal capping devices 100a, 100b. Most preferably, the backspan of each clip 150 is fixedly secured to sternal capping devices 100a.

Preferably, clips 140 and 150 are fixedly secured to sternal capping devices 100a, 100b using known methods and techniques. For example, clips 140, 150 may be welded to, integrally formed with, adhered to, screwed to and/or otherwise fixedly secured to sternal capping devices 100a, 100b. Preferably, clips 140, 150 are fixedly secured to sternal capping devices 100a, 100b in such a manner so as to not readily separate from sternal capping devise 100a, 100b during the surgical procedure.

While the sternal capping devices have been described in connection with what is presently considered to be the most practical and preferred embodiments, it is to be understood that the sternum capping devices are not to be limited to the disclosed embodiments, but on the contrary, it is intended to cover various modifications and equivalent arrangements included within the spirit and scope of the appended claims.

What is claimed is:

1. A device to be independently interposed between an exposed end of a sternal half of a longitudinally divided sternum and a blade of a surgical retractor, the device comprising:
   an end wall having a size and a dimension to at least partially cover the exposed end of a sternal half, wherein the device is independently placeable against the exposed end of the sternal half, wherein the end wall includes a rounded first and second end;
   an upper wall integrally formed with and extending orthogonally from an upper edge of the end wall; and
   a lower wall integrally formed with and extending orthogonally from a lower edge of the end wall, wherein the upper wall and the lower wall extend along the first and second ends of the end wall, wherein the upper wall and the lower wall define a continuous wall around the perimeter of the end wall.

2. The device according to claim 1, further comprising anchoring structure extending from the end wall.

3. The device according to claim 2, wherein the anchoring structure includes at least one spike protruding from a surface of the end wall to contact the exposed end of the sternal half.

4. The device according to claim 3, wherein the spikes are removably connected to the end wall.

5. The device according to claim 4, further comprising a wall extending around at least a portion of the end wall.

6. The device according to claim 1, wherein the end wall is fabricated from at least one of plastic, stainless steel and titanium.

7. The device according to claim 1, wherein the device stanches the effusion of blood from the exposed end of the sternal half.

8. A device for use with a retractor including at least one blade, wherein the device is used for stanching the effusion of blood from an exposed sternal half of a longitudinally divided sternum, formed during a sternotomy, the device comprising:
   an upper wall;
   a lower wall spaced from the upper wall; and
   an end wall interconnecting the upper and lower walls;
      the upper wall, the lower wall and end wall bounding a space; and
      the upper wall and the lower wall defining an opening through which an exposed end of a sternal half is receivable into the space of the device, wherein a respective blade of the retractor engages a surface of the device opposite the space of the device; and
   a first arcuate terminal end and a second arcuate terminal end.

9. The device according to claim 8, wherein the device has one of a "C-shaped" and a "U-shaped" transverse cross-sectional profile.

10. The device according to claim 9, wherein the upper wall, the lower wall and the end wall have a radius of curvature of about 8.625 inches.

11. The device according to claim 9, wherein the upper wall has a thickness of about 0.1875 inches.

12. The device according to claim 11, wherein the lower wall has a thickness of about 0.0625 inches.

13. The device according to claim 9, wherein the upper and lower walls are of equal thickness.

14. The device according to claim 13, wherein the device is fabricated from at least one of a plastic, a polycarbonate, stainless steel and titanium.

15. The device according to claim 13, wherein the space between the upper and lower walls of the device has a height of about 0.75 inches.

16. In a sternotomy wherein the sternum of a patient has been longitudinally incised along at least a portion thereof, thereby exposing and allowing two opposing sternal halves to be separated laterally, the improvement comprising the step of:
   providing a pair of caps for stanching the effusion of blood from the exposed sternal halves of the sternum, each cap comprising:
      an upper wall;
      a lower wall spaced from the upper wall; and
      an end wall interconnecting the upper and lower walls;
         the upper wall, the lower wall and end wall bounding a space;
         the upper wall and the lower wall defining an opening through which the sternal half is receivable into the space of the cap, wherein a blade of a surgical retractor engages a surface of the device opposite the space of the device;
   placing a cap on each exposed sternal half such that the sternal half is received in the space of the cap;
   placing the blades of a surgical retractor, when in an approximated position, between the caps placed over the exposed ends of the sternal halves; and
   manipulating the retractor to separate the blades of the surgical retractor and spread the sternal halves apart.

17. The method according to claim 16, wherein each cap is fabricated from at least one of polycarbonate, stainless steel and titanium.

18. The method according to claim 16, wherein each cap includes at least one spike extending from the end wall thereof.

19. The method according to claim 18, further comprising the steps of:
providing clips for guiding and securing the caps against the exposed ends of the sternal halves; and
placing the clips over the caps and into engagement with the sternal halves.

* * * * *